US00PP35972P3

(12) United States Plant Patent
Bouchet

(10) Patent No.: US PP35,972 P3
(45) Date of Patent: Jul. 9, 2024

(54) WHITE FLAT NECTARINE TREE NAMED 'CAKELINDA'

(50) Latin Name: ***Prunus persica* (L.) Batsch.**
Varietal Denomination: CAKELINDA

(71) Applicant: AGRO SELECTIONS FRUITS, Elne (FR)

(72) Inventor: Christophe Bouchet, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 18/445,622

(22) Filed: Nov. 28, 2023

(65) Prior Publication Data

US 2024/0180050 P1 May 30, 2024

(30) Foreign Application Priority Data

Nov. 29, 2022 (QZ) ..... PBR 2022/2714

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 5/0856
See application file for complete search history.

*Primary Examiner* — Kent L Bell
(74) *Attorney, Agent, or Firm* — Birch, Stewart, Kolasch & Birch, LLP

(57) ABSTRACT

A new and distinct variety of white flat nectarine tree denominated 'CAKELINDA' which have fruits with medium size, high cating quality and very long shelf life without alteration before and after harvesting, with a semi-sweet to balanced white flesh, and an attractive skin with a very high percentage of luminous red to purple red blush on skin surface, on a red background.

4 Drawing Sheets

Botanical classification: *Prunus persica* (L.) Batsch.
Variety denomination: 'CAKELINDA'.

This application claims priority of Community plant variety right No. 2022/2714 filed on Nov. 29, 2022 (11/29/22) which is hereby incorporated by reference in its entirety.

The new variety named 'CAKELINDA' is also known as 23.04.54.19 NBPL or ASF2005. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'CAKELINDA', the provisional reference of this white flat nectarine tree variety was 23.04.54.19, corresponding to the tree 54 located in line 04 of the parcel 23 and selected during the year 2019. The letters "NBPL" are related to the first letters of the type of tree in French (NBPL for "Nectarine Blanche PLate", that means "white flat nectarine"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety ' CAKELINDA', the clone reference was 'ASF2005'.

BACKGROUND OF THE NEW VARIETY

The present invention relates to a new and distinct variety of white flat nectarine tree, *Prunus persica* (L.) Batsch, which has been given the variety denomination 'CAKELINDA'.

This new tree produces fruits with a long shelf life without alteration both on the tree after growth completion and after harvesting, very good eating quality, semi-clingstone white flesh fruits, generally with a red pigmentation under the fruit skin, for fresh market at the end of June or early in July in the Pyrénées-orientales department, France.

ORIGIN OF THE VARIETY

The 'CAKELINDA' white flat nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'CAKELINDA' variety results from pollinated cross between the white flat nectarine variety named 'CAKESNOW' (U.S. Plant Pat. No. 29,886) which was used as the seed parent, or female parent, and the white nectarine variety named '4N.08.157.06NB ASF 0621' (not patented) which was used as the pollen parent, or male parent.

The 'CAKELINDA' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CAKELINDA' white flat nectarine tree blooms at the middle of February near Elne in the Pyrénées-Orientales department, France. The blooming period is considered medium. However, it was observed that its date of blooming seems to be highly dependant on climatic conditions.

The first fruit of 'CAKELINDA' ripens generally early to medium in the season, namely at the middle or at the end of June. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
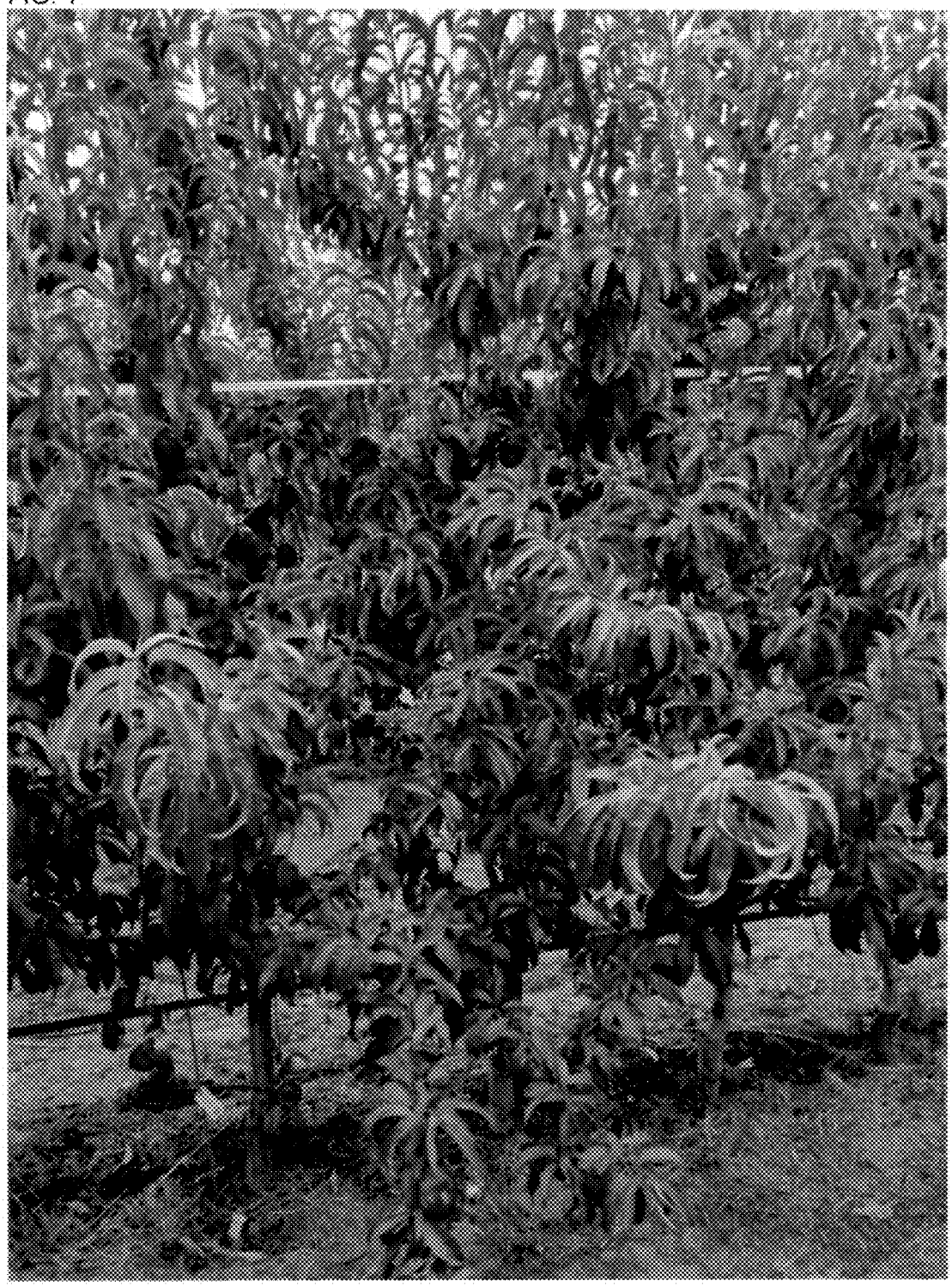
FIG. 1 is a color photograph showing trees of the new variety 'CAKELINDA' in orchard, bearing fruits.
Figure 2:
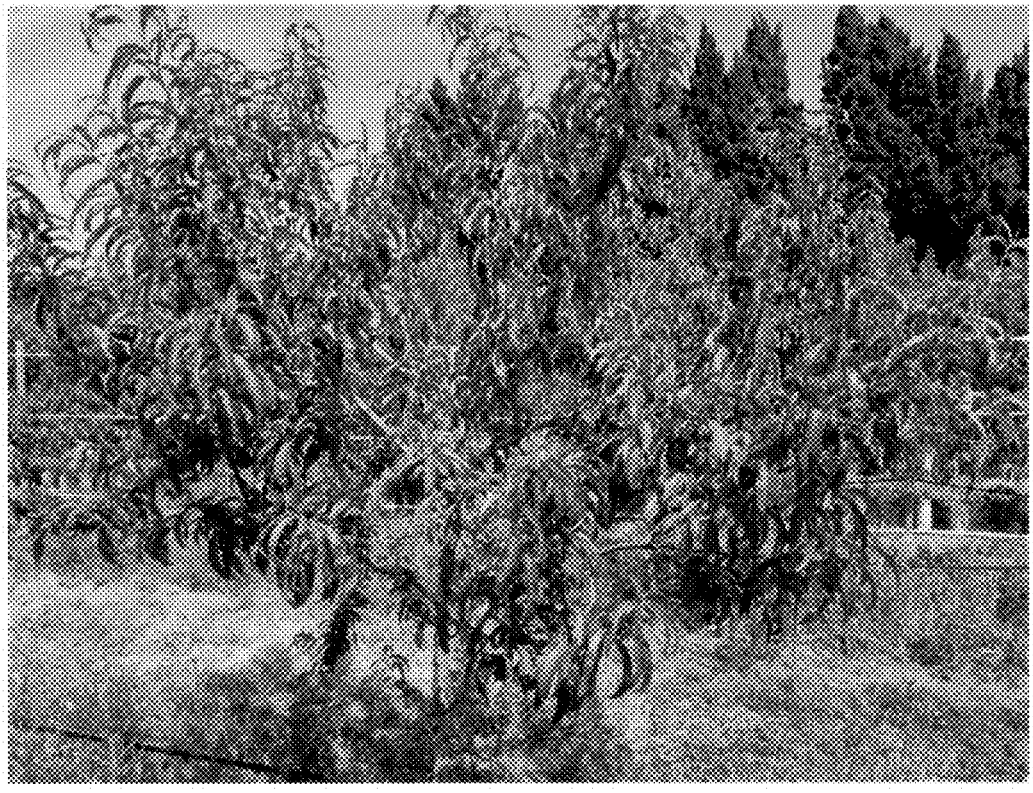
FIG. 2 is a second color photograph showing a tree of the new variety 'CAKELINDA' in orchard, bearing fruits.
Figure 3:
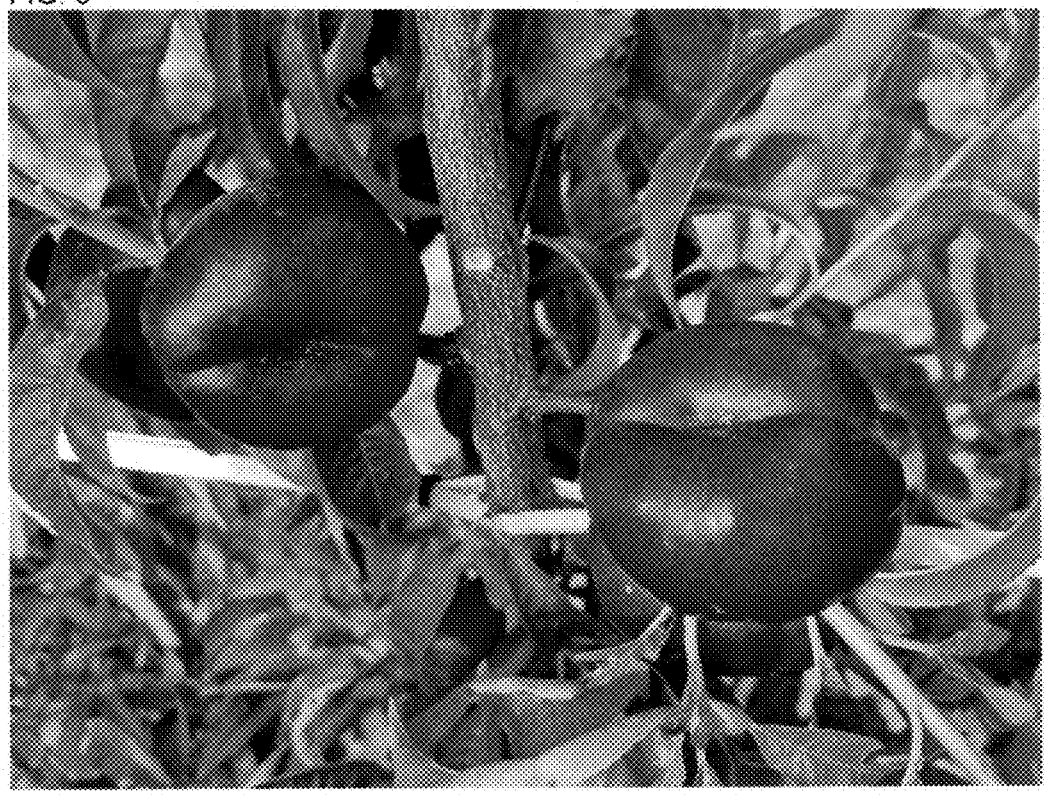
FIG. 3 is a color photograph showing a close view of fruits of the new variety 'CAKELINDA' in orchard, at maturity time.
Figure 4:
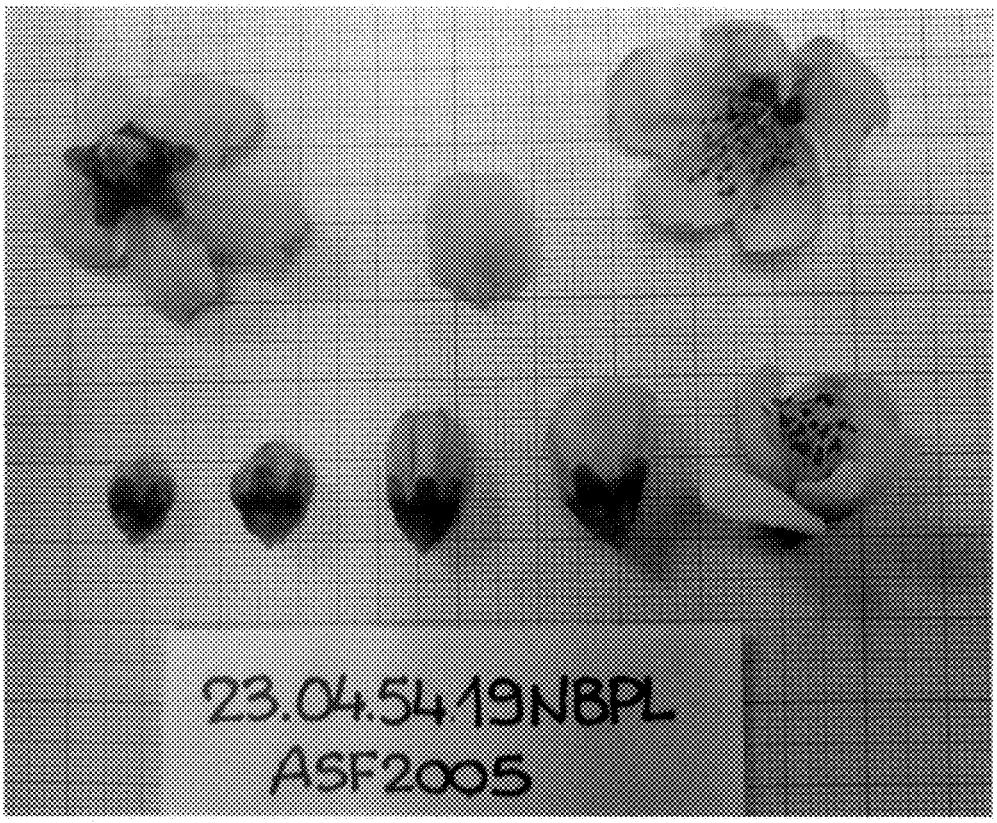
FIG.4 is a color photograph which depicts the flower buds at different development stages, and the reverse and side views of the flower and the reproductive organs with petals removed, of the new variety 'CAKELINDA' also named '23.04.54.19NBPL' or 'ASF2005' as indicated in the figure.
Figure 5:
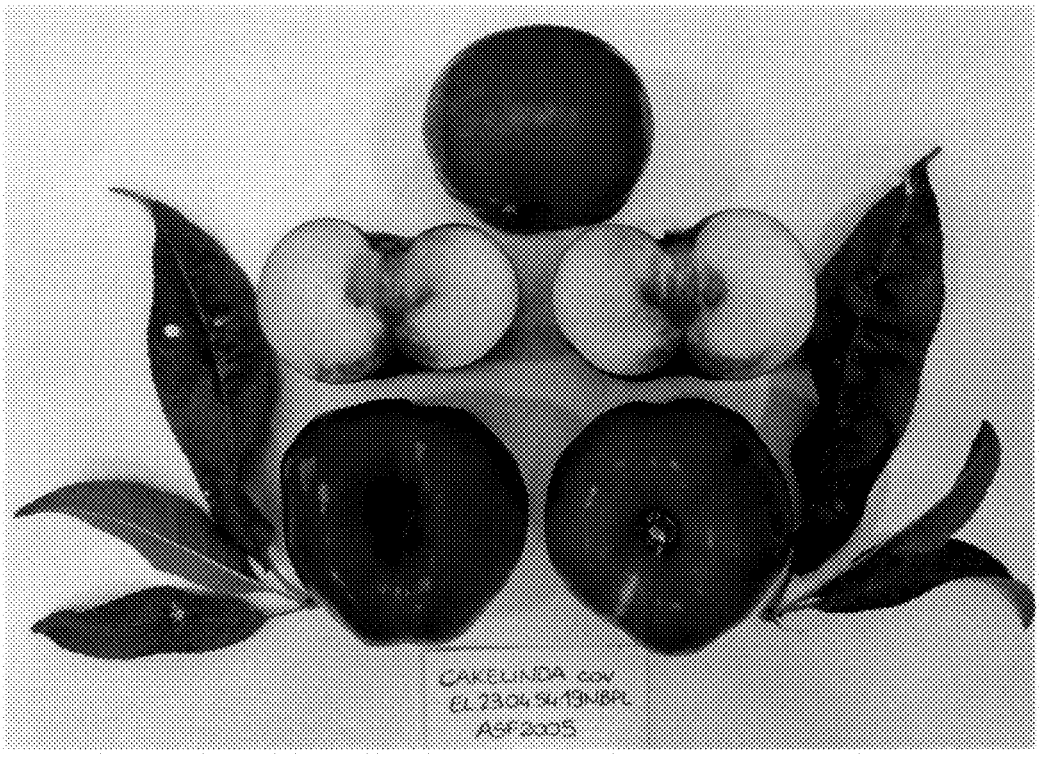
FIG. 5 is a color photograph which shows the upper and lower sides of leaves and different views of four typical specimens of the fruit of the new variety 'CAKELINDA' also named 'EL.23.04.54.19NBPL' or 'CAKELINDA cov' or 'ASF2005', at ripening time, one fruit having been cut in half with the pit being left in one of the halves for depicting leaves, fruit flesh, pit and pit cavity of the new variety.
Figure 6:
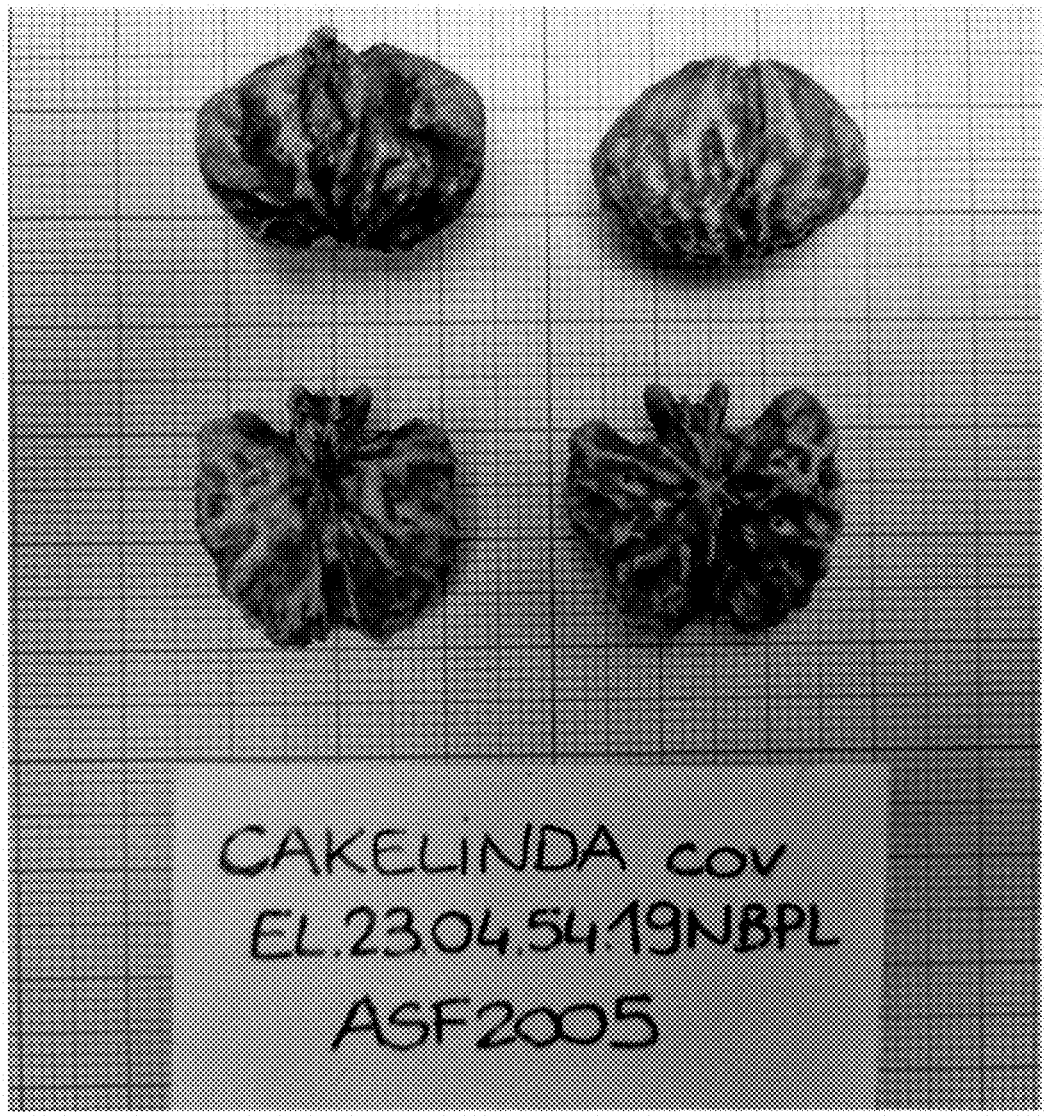
FIG. 6 is a color photograph that shows different views of the stone of the new variety 'CAKELINDA' also named 'EL.23.04.54.19NBPL' or 'CAKELINDA cov' or 'ASF2005' as indicated in the figure.

The views of trees, flowers, leaves and fruits have been photographed in their fourth growing season (third year of production).

Due to chemical development, processing and printing, the flowers, stones and fruits depicted in these photographs may or may not be accurate when compared to the actual botanical specimen.

DETAILED BOTANICAL DESCRIPTION

The trees, flowers, and fruits may vary in slight detail due to variations in soil type, cultural practices, and climatic condition. The potential for commercial production of fresh fruits by 'CAKELINDA' is high, due to fruit very long shelf life without alteration after harvesting.

Trees are medium vigorous and medium to large stature half-standing in semi flared out aspect. The anthocyanic coloration of flowering shoot is present excluding brush-wood side away from sun. The time of beginning of flowering is considered medium; flowering begins at the middle of February. The type of flower is showy (rosette) with medium to large petal size. Petals are pink. Leaf glands are present and reniform or intermediate. The fruit flesh is white with a sparse red pigmentation under the fruit skin. The fruit skin is thin, with a luminous red to purple red blush on a red background. The stone is semi-clingstone and its size is small to medium. Fruit taste is semi-sweet to balanced, aromatic and with a high level of sugars.

Compared to white flat nectarine variety 'CAKEBELLA' (U.S. Plant Pat. No. 29,884), the fruits of the new variety 'CAKELINDA' ripen slightly earlier, of about one to two week. The size of the fruits of the new variety 'CAKELINDA' is slightly smaller than the fruits of the similar variety 'CAKEBELLA'. The fruit taste of the fruits of the new variety 'CAKELINDA' is slightly more acid than the fruit taste of 'CAKEBELLA'.

Compared to white nectarine named 'NECTARBOOM' (U.S. Plant Pat. No. 23,355), the fruits of the new variety 'CAKELINDA' ripen approximately at the same time. The flowers of the fruits of the new variety 'CAKELINDA' bloom about 10 to 12 days earlier than the flowers of the variety 'NECTARBOOM'. The flower type of the new variety 'CAKELINDA' is rosette, whereas the 'NECTARBOOM' variety produces campanulate flowers. It also should be noted that the new variety 'CAKELINDA' produces white flat nectarine fruits, whereas the variety 'NECTARBOOM' produces white nectarines.

Compared to its seed or female parent, i.e. the 'CAKESNOW' (U.S. Plant Pat. No. 29,886) white flat nectarine tree variety, the new variety 'CAKELINDA' ripen approximately two to three weeks earlier. The flowering period of the new variety 'CAKELINDA' also begins earlier than the flowering period of 'CAKESNOW', of about two to three weeks.

Compared to its pollen or male parent, i.e. the '4N.08.157.06NB ASF 0621' (not patented) white nectarine variety, the new variety 'CAKELINDA' produces flat fruits. The fruits of the new variety 'CAKELINDA' ripen approximately 14 days later than the fruits of the parent variety '4N.08.157.06NB ASF 0621'. The flowers of the new variety 'CAKELINDA' blooms approximately 12 days later than the flowers of the parent variety '4N.08.157.06NB ASF 0621'.

DETAILED DESCRIPTION

Referring more specifically to the pomological details of this new and distinct variety of white flat nectarine tree, the following was observed on trees in their fourth growing season (third year of production), except for the observations done on flowers (third growing season), under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

TREE

Size:

*Generally*.—Considered medium to large. The tree size the first year was approximately 200 to 280 cm in height. The tree was pruned during each following dormant season to a height of approximately 250 cm. Current season shoots growth could reach 80 cm in length. The tree size from the second year (second and next years) reached a final height of 330 cm including current season shoots length. The tree size is consistently reduced to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered medium.

Productivity: Considered good to very good, and regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to monilia or rot are significantly reduced. 'CAKELINDA' variety is not much sensitive to cracking of pistil cavity, to cork formation into peduncle cavity or to monilia.

Bearer: Very regular. The fruit distribution is considered homogenous on mixed branches and spurs having more than 1 year. Thinning of 2 fruits out of 3 was necessary for the tree valorisation. Thinning was necessary every year during the years of observation.

Form: The 'CAKELINDA' variety has naturally a semi-flared shape.

Density: Considered dense.

Tree branching: Medium to strong.

Hardiness: The present tree was grown and evaluated in France. The variety appears to be hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017, 1017 hours in 2017-2018, 844 hours in 2018-2019, 706 hours in 2019-2020, 822 hours in 2020-2021, 700 hours in 2021-2022 and 919 hours in 2022-2023, showed a good behavior of the tree in all cases. No injury with temperatures as low as −12° C. in winter. Good resistance to late frosts.

TRUNK

Diameter: Approximately 41.0 to 46.0 millimeters in diameter when measured at a distance of approximately 20.0 centimeters above the soil level for trees on fourth leaves (or third year of production)

Bark texture: Considered rough, with lenticels.

Lenticels: Numerous lenticels are present. The number of lenticels reaches 2 lenticels per $cm^2$. The lenticels range in size of approximately 4.0 to 5.0 millimeters in width, and about 1.0 to 1.5 millimeters in height.

Lenticel color: The lenticels show a beige color (RHS Greyed Orange N167 C).

Bark coloration: The bark has a brown (RHS Grey Brown 199 B) to grey color (RHS Grey 201 C or RHS Grey 201 D), darker than the lenticels color.

BRANCHES

Size: The branches are pruned to approximately 1.0 meter in length.

Diameter: Average as compared to other nectarine varieties. The current season shoots have a diameter of approximately 4.0 to 6.0 millimeters, and mature branches have a diameter of approximately 8.0 to 10.0 millimeters.

Surface texture: Smooth, despite the presence of small lenticels, for current season shoots and rough, with lenticels for mature branches, wood which is several years old has no furrowed appearance.

Crotch angles: Primary branches are considered variable, but the crotch angles are generally 45 degrees from the horizontal axis for current season shoots and 65° degrees from the horizontal axis for mature branches. This particular characteristic is not considered distinctive of the variety, however.

Current season shoots:

Internode length: Generally 17.0 to 22.0 millimeters.

*Color*.—The color of new shoot tips is considered light green (RHS Yellow Green 144 A or RHS Yellow Green 144 B) on lower part of new shoot tips, whereas the upper part is darker and colored in purple (RHS Greyed Red 182 A or RHS Greyed Red 182 B), depending on the level on the tip and the sunlight exposure.

Mature branches:

Internode length: Generally 20.0 to 28.0 millimeters.

Color of mature branches: Brown (RHS Grey Brown 199 A or RHS Grey Brown N199 C).

Lenticels: Numerous lenticels are present on mature branches. The number of lenticels reaches 0.5 lenticels per $cm^2$. The size of lenticels is considered small on one-year old shoots and on two-year-old shoots. The lenticels range in size from approximately 1.0 to 1.5 millimeter in diameter, both on one year's old shoots and on two-year-old shoots. The lenticel shape is considered stretched round on one-year old shoots and stretched round on two-year-old shoots. The lenticels may have a height of 1.0 millimeter and a width of 2.0 millimeters on mature branches.

Lenticel color: The lenticels have a beige color (RHS Greyed Orange N167 C).

LEAVES

Time of beginning of leaf bud burst: Considered medium.

Size: Considered medium for the species. The ratio leaf length/leaf width is 3.592.

Leaf length: The medium length is about 136.5 millimeters with leaf petiole.

Leaf width: The medium width is 38.00 millimeters.

Leaf form (in cross section): Concave.
Leaf form: Entire.
Leaf base shape: Acute.
Leaf tip form: Acute.
Leaf thickness: Medium.
Leaf color:
*Upper leaf surface*.—Green (RHS Yellow Green 177 A).
*Lower surface*.—A slightly lighter green (RHS Yellow Green 146 A) than the upper leaf surface color.
Leaf texture: Smooth and glabrous on both upper and lower surfaces of the leaf.
Leaf venation: Pinnately veined.
Mid-vein:
*Color*.—Light green (RHS Yellow Green 145 A).
*Width*.—Approximately 1.0 millimeter.
Secondary veins:
*Color*.—Light green (RHS Yellow Green 145 B).
Leaf margins: Slightly undulating.
Form: Considered denticulate.
Uniformity: Leaves are isolated or grouped by 2 or 3. In this last case, one leaf of normal size is found with one or two smaller leaves (at least 50% smaller).
Leaf petioles:
*Size*.—Considered medium.
*Length*.—About 12.0 to about 16.0 millimeters.
*Diameter*.—About 1.7 to 2.0 millimeters.
*Shape*.—Grooved.
Petiole color:
*Upper petiole surface*.—Green (RHS Yellow Green 144 A).
*Lower surface*.—A slightly lighter green (RHS Yellow Green 145 A or RHS Yellow Green 145 B) than the upper petiole surface color.
*Ratio leaf length/petiole length*.—Approximately 9.
Leaf glands:
*Size*.—Considered medium. Their length is about 2.0 millimeters and their width is about 1.0 millimeter.
*Number*.—Generally 2 glands per leaf, sometimes 3.
*Type*.—Reniform to intermediate.
*Margins*.—Smooth.
*Position*.—Alternate on the upper part of petiole.
*Color*.—On young leaves, leaf glands color is considered a light green (RHS Yellow Green N144 A or RHS Yellow Green N144 B). On older leaves, leaf glands color turns to a brown (RHS Brown N200 A) color.
Leaf stipules:
*Generally*.—Leaf stipules have been observed. Stipules are in pairs, medium in size, and with a green color (RHS Yellow Green NN137 A). But as seen in the characteristic relative to the leaves uniformity, it is possible to find leaves by groups of 2 or 3, with a normal-size leaf and smaller ones.

FLOWERS

Flower buds:
*Generally*.—At pre-floral stage of development, the floral buds are conic in shape. Their form is evolving until blooming, with variable dimensions. Just before blooming, floral buds are approximately 7.0 to 8.0 millimeters wide and approximately 10.0 to 12.0 millimeters long. The floral buds show a homogenous distribution on the trees.
*Color*.—This characteristic is dependent upon the proximity to bloom. At pre-floral stage of development, the bottom of the flower's buds, or calyx, or flower receptacle, is of purple color (RHS Greyed Purple 187 A) on its outer face. The inner face of the flower receptacle is green and slightly orange (RHS Yellow Green 153 B or RHS Yellow Green 153 C). The corolla, formed by the petals, is generally pink colored (RHS Red Purple 63 A) on both faces. Petals color shows an evolution until the end of flowering.
Hardiness: The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.
Date of bloom: The blooming time generally begins around the middle of February. The first bloom was observed on Feb. 10, 2020.
Blooming time: Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus, the full bloom was observed in 2020, from February $10^{th}$ until February $17^{th}$, then from February $11^{th}$ until Feb. 22, 2021, and then from February $10^{th}$ until Feb. 19, 2022.
Duration of bloom: Medium, approximately between 8 to 12 days. This characteristic varies slightly with the prevailing climatic conditions.
Flower type: The variety is considered to have a showy type flower.
Flower size: Considered medium. Flower diameter at full bloom is approximately 32.0 to 36.0 millimeters.
Bloom quantity: Considered high, approximately 40 to 45 flowers per meter, with a high rate of fruit set.
Flower bud frequency: Generally 2 or 3 flower buds appear per node, occasionally 1.
Petal size:
*Generally*.—Considered medium to large.
Length: Generally between 17.0 and 19.0 millimeters.
Width: Generally between 16.0 and 17.0 millimeters.
Petal form: Round-shaped.
Petal count: Usually 5.
Petal arrangement: Overlapping.
Petal texture: Smooth on both upper and lower surfaces of the petal.
Petal color: At the stage F of blooming, when the flower is fully opened, both surfaces of the petal are colored with a pink (RHS Red Purple 62 C) color when young, becoming slightly darker until the end of blooming.
Fragrance: Moderate, floral fragrance.
Petal claw:
*Form*.—The claw is considered to have a narrow form.
*Length*.—About 1.0 to 1.5 millimeters.
*Width*.—About 1.0 millimeter at the base.
*Color*.—The petal claw usually shows a pink color darker than the petal color (RHS Red Purple 61 A).
Petal margins: Generally considered slightly undulating.

Petal apex:
*Generally*.—The petal apices are generally shaped as a wide dome.
Flower pedicel:
*Length*.—Considered small and having an average length of approximately 1.5 to 2.5 millimeters.
*Diameter*.—Considered average, approximately 1.0 to 1.5 millimeters.
*Color*.—Green (RHS Yellow Green 145 A).
Calyx:
*Internal surface texture*.—Smooth.
*Color*.—At the stage F of blooming, when the flower is opened, the inner surface of the calyx, namely the flower receptacle, is greenish yellow (RHS Greyed Orange 163A or RHS Greyed Orange 163 B) to light orange (RHS Yellow Orange 22 B). The outer surface of the calyx is considered of purple color (RHS Greyed Purple 183 A).
Sepals:
Sepal count: Usually 5 sepals.
*Surface texture*.—The outer surface has a short, fine pubescent texture.
*Margins*.—Smooth.
*Size*.—Medium.
*Length*.—Approximately 4.0 to 6.0 millimeters.
*Width*.—Approximately 4.0 to 5.0 millimeters.
*Form*.—Conic and round at the top.
*Color*.—The upper surface of the sepals shows a purple color (RHS Greyed Purple 183 A) whereas the lower surface of sepals is considered green (RHS Yellow Green 144 A or RHS Yellow Green 146 B).
Anthers:
*Generally*.—Small in length, approximately 1 millimeter.
*Shape*.—Reniform.
*Color*.—Depending on the maturity stage, anthers are colored with a red (RHS Greyed Purple 185 A) to a yellow color (RHS Yellow 12 A).
Pollen production: Pollen is abundant and has a yellow color (RHS Yellow Orange 16 A). The present variety is considered auto-fertile (self-pollinating).
Pistil:
*Number*.—Usually 1.
*Generally*.—Average in size.
*Position*.—The pistil is positioned below the stamens.
*Length*.—Approximately 13.0 to 16.0 millimeters including the ovary. Generally smaller than filaments in length when considered without the ovary.
*Color*.—Considered light green (RHS Yellow Green 145 C).
Ovary:
*Height*.—Approximately 1.5 to 2.0 millimeters.
*Diameter*.—Approximately 1.0 to 1.5 millimeters.
*Color*.—Green (RHS Yellow Green 145 A).
*Pubescence*.—Absent.
Stamens:
*Size compared to petals*.—The size of stamen is smaller than the size of petals.
*Length*.—Approximately 14.0 to 17.0 millimeters, higher than the pistil length.
*Color*.—White (RHS White N 155 B) to slightly pink (RHS Red 51 C) depending on the maturity stage.
Average number of stamens per flower: Approximately 43 to 49 stamens per flower.
Stigma:
*Diameter*.—Approximately 1.0 millimeter.
*Color*.—Yellowish (RHS Yellow Green 153 A or RHS Yellow Green 153 B).
*Shape*.—Round.
*Position of the stigma compared to the anthers*.—Below.

FRUIT

Maturity when described: Firm in ripe conditions (shipping ripe).
Date of first picking: Jun. 11, 2020.
Date of last picking: The date of harvest varies slightly with the prevailing climatic conditions. The 'CAKELINDA' variety has an early to medium season date of picking, and a grouped maturity. The maturity is grouped within 7 to 9 days and the harvest is generally performed in two runs. Last known picking times carry on from June 11$^{th}$ to Jun. 18, 2020, then from June 24$^{th}$ to Jul. 2, 2021, then from June 15$^{th}$ to Jun. 23, 2022, and then from June 22$^{nd}$ to Jun. 28, 2023.
Size:
*Generally*.—Homogeneous in size, size A to 2A. Considered medium.
Average cheek diameter: Approximately 67.0 to 70.0 millimeters.
Average axial diameter: Approximately 43.0 to 45.0 millimeters.
Thickness: Approximately 65.0 millimeters.
Typical weight: Approximately 115.60 grams. This characteristic is high dependent upon the prevailing cultural practices, and therefore is not particularly distinctive of the variety.
Fruit form:
*Generally*.—Flat in shape. The fruit is generally uniform in symmetry, viewed from the suture's plane, and regular.
Suture:
Fruit suture: The suture is usually flared and slightly marked, extending from the base to the apex. No apparent callousing or stitching exists along the suture line, which is uniform. Not pointed.
Color: Purple red (RHS Greyed Purple 185 A).
Ventral surface:
*Form*.—Smooth.
Apex: Slightly depressed.
*Mucron*.—Absent.
*Closing of the pistil cavity*.—Very good. The pistil cavity is almost not visible.
Stem cavity: Average depth of the stem cavity is considered medium, about 6.0 to 8.0 millimeters. Average width is between 15.0 and 17.0 millimeters, and the stem cavity is flared.
Fruit skin:
*Thickness*.—Considered thin and strong, and the skin is adherent to flesh is strong.
*Texture*.—The pubescence of the skin absent, the skin is smooth and glabrous, and shiny.
*Taste*.—Semi-sweet.
*Tendency to crack*.—None observed.
Color:
*Blush color*.—This blush color is a luminous red to purple red (RHS Greyed Purple 185 A or RHS Greyed Purple 187 B). The solid purple red blush covers approximately 95% of the fruit skin surface on a red background (RHS Red 45 A) on approximately 5% of the fruit skin surface. The percentage of the blush on the fruit skin surface can vary and is generally dependent upon the prevailing conditions under which the fruit was grown. The pattern of over color of skin is a solid flush.

*Ground color*.—The ground color covers approximately 5% of the fruit skin surface, and is considered red (RHS Red 45 A).

*Lenticels*.—Some rare lenticels are present. Lenticels are round, with a diameter of approximately 1.0 millimeter, and beige colored (RHS Greyed Yellow 161 A).

Fruit stem: Short in length. Approximately 4.0 to 6.0 millimeters in length. No tearing or detachment.

Diameter: Approximately 4.0 to 5.0 millimeters.

Color: Pale green (RHS Yellow Green 145 A).

Flesh:

*Ripens*.—Very homogenously, slowly. Grouped maturity.

*Texture*.—Firm, crunchy, melting, before maturity stage.

*Fibers*.—Not fibrous.

*Aroma*.—Considered present, with no further characterization.

*Eating quality*.—Considered good, semi-sweet to balanced, sugary, aromatic.

*Flavor*.—Considered semi-sweet to balanced. The Brix is generally superior to 10.0, and acidity is medium to low.

*Juice*.—Juicy at complete maturity. The juice is usually colourless or slightly cream color (RHS NN155 D).

*Brix*.—Generally between 10.2 and 11.6 degrees. The medium Brix is 11.0 degrees. This characteristic varies slightly with the number of fruits per tree, prevailing cultural practices and the surrounding climatic conditions.

*Flesh color*.—The flesh is considered white (RHS White 155 D), with the same color around the stone cavity.

*Red coloration of flesh next to skin*.—Sparse (RHS Red N45 C).

STONE

Type: Semi-Clingstone, more or less semi-adherent depending on the fruit maturity.

Size: Considered small to medium for the variety. The stone size varies significantly depending upon the tree vigor, crop load and prevailing growing conditions.

Length: Approximately 21.0 to 22.0 millimeters.

Width: Approximately 23.0 to 24.0 millimeters.

Diameter: Approximately 15.0 to 16.0 millimeters.

Form: Flattened.

Base: Straight.

Apex:

*Shape*.—Not marked.

*Shape of stem tip*.—Flattened.

Stone cavity: Considered small in size, with flattened form similar to the stone form, and dimensions corresponding to the stone dimensions (approximately 21.0 to 22.0 millimeters in length, 23.0 to 24.0 millimeters in width and 15.0 to 16.0 millimeters in diameter).

Stone surface:

*Surface texture*.—The pit is transversely furrowed on its entire surface. Furrows are deeper and more oblate on lateral sides.

*Ridges*.—The surface texture is generally characterized by more prominent ridges along the ventral edges and at the apical tip.

Ventral edge:

*Width*.—Narrow. Approximately 2.5 millimeters at mid-suture.

Dorsal edge:

*Shape*.—Grooved.

Stone color: The color of the dry stone is generally considered light brown (RHS Greyed Yellow 161 A or RHS Greyed Yellow 161 B) to dark brown (RHS Greyed Orange 165 B).

Tendency to split: Splitting is absent.

Kernel:

*Size*.—The kernel is considered small.

*Length*.—Approximately 8.0 to 9.0 millimeters.

*Width*.—Approximately 7.0 to 8.0 millimeters.

*Thickness*.—Approximately 7.0 to 8.0 millimeters.

*Form*.—Considered round.

*Pellicle*.—The pellicle of the kernel is smooth.

*Color*.—The kernel skin is brown colored (RHS Greyed Orange 165 B). The almond, which is the seed of the kernel, is white (RHS White NN 155 B) and has a sweet taste. The kernel and its embryo are mature at the time of fruit maturity.

Use: The subject variety 'CAKELINDA' is considered to be a white flat nectarine tree having an early to medium season of maturity, and which produces fruits that are considered firm, attractively colored in purple red. Fruits have semi-sweet to balanced taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

Keeping quality: Remarkable. Fruits have a slow maturation and a long shelf life both on the tree after growth completion and after harvesting without alteration. After growth completion, fruits are preserved more than one week. After harvest, fruits are well preserved more than 2 weeks at 2.0 degree Celsius.

Shipping quality: Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

Resistance to insects and disease: No particular susceptibilities were noted. The present variety is not very sensitive to Monilia or rot. The pistil cavity is completely closed, generally without any cork formation.

Although the new variety of white flat nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white flat nectarine tree named 'CAKELINDA' as illustrated and described, characterized by fruits with medium size, high eating quality and very long shelf life without alteration before and after harvesting, with a semi-sweet to balanced white flesh, and an attractive skin with a very high percentage of luminous red to purple red blush on skin surface, on a red background.

* * * * *